(12) United States Patent
Petereit et al.

(10) Patent No.: US 8,343,542 B2
(45) Date of Patent: Jan. 1, 2013

(54) METHOD FOR PRODUCING AN IMMEDIATELY DECOMPOSING ORAL FORM OF ADMINISTRATION WHICH RELEASES ACTIVE INGREDIENTS

(75) Inventors: Hans-Ulrich Petereit, Darmstadt (DE); Christian Meier, Darmstadt (DE); Andreas Gryczke, Griesheim (DE)

(73) Assignee: Evonik Roehm GmbH, Darmstat (DE)

( * ) Notice: Subject to any disclaimer, the term of this patent is extended or adjusted under 35 U.S.C. 154(b) by 995 days.

(21) Appl. No.: 10/542,283

(22) PCT Filed: Nov. 21, 2003

(86) PCT No.: PCT/EP03/13059
§ 371 (c)(1),
(2), (4) Date: Jul. 15, 2005

(87) PCT Pub. No.: WO2004/066976
PCT Pub. Date: Aug. 12, 2004

(65) Prior Publication Data
US 2006/0051412 A1    Mar. 9, 2006

(30) Foreign Application Priority Data
Jan. 28, 2003  (DE) ................................. 103 04 403

(51) Int. Cl.
*A61K 9/20* (2006.01)
*B27N 3/00* (2006.01)
(52) U.S. Cl. ........................................ 424/464; 264/109
(58) Field of Classification Search .................. 424/464; 264/109
See application file for complete search history.

(56) References Cited

U.S. PATENT DOCUMENTS

| | | | |
|---|---|---|---|
| 5,529,800 A * | 6/1996 | Bourns et al. | 426/572 |
| 6,194,000 B1 * | 2/2001 | Smith et al. | 424/458 |
| 6,576,255 B1 | 6/2003 | Petereit et al. | |
| 6,656,492 B2 * | 12/2003 | Kajiyama et al. | 424/434 |
| 2002/0168404 A1 | 11/2002 | Rault et al. | |
| 2003/0064036 A1 * | 4/2003 | Petereit et al. | 424/49 |
| 2004/0249035 A1 | 12/2004 | Petereit et al. | |
| 2004/0253314 A1 | 12/2004 | Petereit et al. | |

FOREIGN PATENT DOCUMENTS

| | | |
|---|---|---|
| EP | 0 417 588 | 3/1991 |
| WO | 01/39751 | 6/2001 |
| WO | 02/067906 | 9/2002 |
| WO | 03/007917 | 1/2003 |

OTHER PUBLICATIONS

U.S. Appl. No. 12/159,538, filed Jun. 27, 2008, Meer, et al.
Canadian Office Action issued Dec. 2, 2011, in Patent Application No. 2,512,738.

* cited by examiner

*Primary Examiner* — Aradhana Sasan
(74) *Attorney, Agent, or Firm* — Oblon, Spivak, McClelland, Maier & Neustadt, L.L.P.

(57) ABSTRACT

The invention relates to a method for producing an oral form of administration which decomposes immediately and releases active ingredients in the mouth. According to said method, (a) an anionic pharmaceutical active ingredient is intensively mixed with (b) a copolymer consisting of radically polymerized $C_1$-$C_4$ esters of the acrylic acid or methacrylic acid and other (meth)acrylate monomers containing functional tertiary amino groups, and (c) between 5 and 50 wt. %, in relation to (b), of a $C_{12}$-$C_{22}$ carboxylic acid in the melted mass; the mixture is solidified and ground to form a powder containing active ingredients having an average particle size of 200 µm or less; and the powder is encapsulated in a water-soluble matrix consisting of pharmaceutically standard adjuvants, on the condition that no more than 3 wt. %, in relation to the copolymer, of emulsifiers with an HLB value of at least 14 must be contained therein. The invention also relates to the powder containing active ingredients and the uses of the same.

19 Claims, No Drawings

METHOD FOR PRODUCING AN IMMEDIATELY DECOMPOSING ORAL FORM OF ADMINISTRATION WHICH RELEASES ACTIVE INGREDIENTS

FIELD OF THE INVENTION

The invention relates to a method for producing an oral pharmaceutical form with immediate disintegration and active ingredient release even in the mouth. The invention further relates to an active ingredient-containing powder and to the use thereof.

PRIOR ART

EP-A 0 417 588 describes a method for producing a complexed medicament composed of an ionic active ingredient by reacting the active ingredient with a complementarily ionic, particulate polymer in the presence of an amount of water sufficient to moisten the mixture. In the case of active ingredient salts it is necessary to add an acid or base to a mixture to neutralize the counter-ion of the active ingredient. For example, sodium carbonate is added to the mixture in the reaction of active ingredient salts such as propranolol HCl, verapamil HCl or metoclopamide HCl with anionic, (meth)acrylate copolymers such as Eudragit® L or Eudragit® L100-55. Taste-masking of the bitter-tasting active ingredients can be achieved in this case. It is additionally mentioned that where the ionic active ingredient is an acid it is possible to employ a particulate polymer which has lateral amino groups as complementarily ionic groups. The lateral amino groups may be for example a tertiary amino group derived from polymerized monomers such as, for example, 2-dimethylaminoethyl methacrylate.

WO 01/39751 describes a method for producing molded articles by injection molding with the method steps a) melting of a (meth)acrylate copolymer which is composed of 30 to 80% by weight free-radical polymerized C1 to C4 alkyl esters of acrylic or methacrylic acid and 70 to 20% by weight (meth)acrylate monomers with a tertiary ammonium or amino group in the alkyl radical, where the (meth)acrylate copolymer is mixed with 1 to 70% by weight of a plasticizer and of dryer in the ratio of 1:1 to 1:20, where at least 1% by weight plasticizer is present, and 0.05 to 5% by weight of a release agent are present, additionally further usual additives or excipients and, where appropriate, an active pharmaceutical ingredient may be present in the mixture, and the mixture has before the melting a content of low-boiling ingredients with a vapor pressure of at least 1.9 bar at 120° C. of more than 0.5% by weight b) degassing the mixture in the plastic state at temperatures of at least 120° C., thus reducing the content of low-boiling ingredients with a vapor pressure of at least 1.9 bar at 120° C. to a maximum of 0.5% by weight, c) injecting the molten and degassed mixture into the mold cavity of an injection mold, the mold cavity having a temperature which is at least 10° C. below the glass transition temperature of the (meth)acrylate copolymer, cooling the melt mixture and removing the resulting molded article from the mold.

WO 02/67906 describes a method for producing a coating and binding agent for oral or dermal pharmaceutical forms consisting essentially of (a) a copolymer consisting of free-radical polymerized C1 to C4 esters of acrylic or methacrylic acid and further (meth)acrylate monomers which have functional tertiary ammonium groups, where the copolymer is in powder form with an average particle size of 1-40 µm, (b) 3 to 15% by weight, based on (a), of an emulsifier having an HLB of at least 14 and (c) 5 to 50% by weight, based on (a), of a $C_{12}$ to $C_{18}$ monocarboxylic acid or of a $C_{12}$ to $C_{18}$ hydroxyl compound, where components (a), (b) and (c) are blended or mixed together with or without addition of water and, where appropriate, with addition of an active pharmaceutical ingredient and further conventional additives, and the coating and binding agent is produced from the mixture by melting, casting, spreading, spraying or granulating.

It is possible according to WO 02/67906 to obtain pharmaceutical forms which are particularly stable on storage and may comprise in particular moisture-sensitive active ingredients such as acetylsalicylic acid, carbenoxolone, cefalotin, epinefrine, imipramine, potassium iodide, ketoprofen, levodopa, nitrazepam, nitroprusside, oxitetracycline HCl, promethazine, omeprazole or other benzimidazole derivatives or streptomycin.

Classes of active ingredients and substances which may often cause a bitter taste and can advantageously be formulated with masking of the taste using the coating and binding agent disclosed in WO 02/67906 are, for example:

analgesics and antirheumatics: paracetamol, diclofenac, aceclofenac, ibuprofen, ketoprofen, flubiprofen, levacetylmethadol, oxycodone psychoactive drugs: prometazines, donepezil, modafinil, nefazodone, reboxetine, sertindole, sertraline antibiotics: erythromicyn, roxithromycin, clarithromycin, grepafloxacin, ciprofloxacin, levofloxacin, sparfloxacin, trovafloxacin, nevirapine beta-blockers: propanolol, metoprolol, bisoprolol, nebivolol antidiabetics: metformin, miglitol, repaglinide H1 antihistamines: diphenhydramine, fexofenadine, mizolastine H2 antihistamines: cimetidine, nizatidine, ticlopidine, cetridine, ranitidine, Vitamins: thiamine nitrates;

and further active ingredients: quinidine sulfate, amiloprilose HCl, pseudoephedrine HCl, sildenafil, topiramate, granisetron, rebamipide, quinine HCl Problem and Solution One problem with many oral pharmaceutical forms is that liquid, e.g. a mouthful of water, is often necessary to assist swallowing. This is unfavorable if, in case of need, no beverage is available or, for example, the current occupational activity must be interrupted in order to be able to take the medicament. Moreover, for many patients it is unpleasant to take their medicament in the presence of other people as it were under observation and attracting attention, this being all the more noticeable if it is necessary to use after a beverage or even ask for one for this purpose.

Many patients, particular mention being made of elderly people and children, therefore desire oral pharmaceutical forms which can be taken simply and unobtrusively virtually anywhere. This is particularly the case with diseases which should or must be taken at a particular time or without delay when required, such as, for example, with analgesics.

There is additionally a need for pharmaceutical forms which on oral intake release the active ingredient present, e.g. analgesic, even in the mouth and, in this way, can have a rapid effect. Known administration forms are, for example, compressed tablets or suckable tablets, freeze-dried tablets, cast tablets or pastilles, sachets, chewable tablets, powders for reconstitution and/or liquid-filled lozenges.

Many of the rapidly disintegrating pharmaceutical forms have the disadvantage, however, that they cause a sandy taste in the mouth which may persist for some minutes until the tablet ingredients have completely dissolved. The sandy taste in the mouth is felt to be unpleasant and may cause an urge to cough. A further problem in this connection is masking the taste of active ingredients with a bitter taste. The known taste-masking coatings cannot be used because of the requirement for release of active ingredient in the mouth.

The intention was to solve these problems by providing a pharmaceutical form which can be taken without liquid and releases the active ingredient immediately. It is moreover intended that there be no sandy taste in the mouth. The pharmaceutical form is to be suitable for a large number of active ingredients, but especially for analgesics of the antirheumatic class or for antibiotics.

The problem is solved by a method for producing an oral pharmaceutical form with immediate disintegration and active ingredient release even in the mouth, by vigorously mixing
  (a) an anionic active pharmaceutical ingredient with
  (b) a copolymer consisting of free-radical polymerized $C_1$ to $C_4$ esters of acrylic or methacrylic acid and further (meth)acrylate monomers which have functional tertiary amino groups, and
  (c) 5 to 50% by weight, based on (b), of a $C_{12}$ to $C_{22}$ carboxylic acid
in the melt, solidifying the mixture and grinding to an active ingredient-containing powder with an average particle size of 200 µm or less, incorporating the powder into a water-soluble matrix of pharmaceutically customary excipients, with the proviso that not more than 3% by weight, based on the copolymer, of emulsifiers having an HLB of at least 14 may be present.

In a manner which is not yet understood, the advantages of the invention are, unlike the case of WO 02/67906, evident only with anionic active ingredients. It is possible that there is a thermally induced interaction of the claimed ingredients (a), (b) and (c) which is not inferable in this way from WO 02/67906. The pharmaceutical forms obtainable according to the invention can easily be taken without additional liquid and do not cause a sandy taste after active ingredient release in the mouth.

Implementation of the Invention

The invention relates to a method for producing an oral pharmaceutical form with immediate disintegration and active ingredient release even in the mouth, by vigorously mixing
  (a) an anionic active pharmaceutical ingredient with
  (b) a copolymer consisting of free-radical polymerized $C_1$ to $C_4$ esters of acrylic or methacrylic acid and further (meth)acrylate monomers which have functional tertiary amino groups, and
  (c) 5 to 50% by weight, based on (b), of a $C_{12}$ to $C_{22}$ carboxylic acid
in the melt, solidifying the mixture and grinding to an active ingredient-containing powder with an average particle size of 200 µm or less, incorporating the powder into a water-soluble matrix of pharmaceutically customary excipients, with the proviso that not more than 3% by weight, based on the copolymer, of emulsifiers having an HLB of at least 14 may be present.

Active Pharmaceutical Ingredient (a)

The anionic active pharmaceutical ingredient is, owing to the production in the melt, present incorporated in the copolymer in the form of a solid solution. The solid solution state can be detected for example under a polarizing microscope, by thermal analysis (differential scanning calorimetry (DSC)) or in the X-ray diffraction spectrum.

The ratio of amounts based on % by weight of active ingredient to copolymer is favorably from 2:1 to 1:2. The copolymer is preferably present in equal amounts or in excess.

The anionic active ingredient (a) is preferably an anionic analgesic, an anionic antirheumatic or an anionic antibiotic.

The active ingredient-containing powder may comprise for example the following anionic active ingredient: acamprosate, aceclofenac, acemetacin, acetylcysteine, acetylsalicylic acid, acetyltyrosine, acipimox, acitretin, alanine, alendronic acid, amethopterin, amino acids, amoxicillin, ampicillin, ascorbic acid, atorvastatin, azidocillin, aztreonam, bacampicillin, baclofen, benazepril, bendamustine, benzylpenicillin, bezafibrate, biotin, bornaprine, bumetamide, cabastine, canrenoic acid, carbamoylphenoxyacetic acid, carbidopa, carbimazole, carbocisteine, carisoprodol, cefaclor, cefadroxil, cefalexin, cefazolin, cefepime, cefetamet, cefixime, cefotaxime, cefotiam, cefoxitin, cefpodoxime, ceftazidime, ceftibuten, ceftriaxone, cefuroxime, cetirizine, chenodeoxycholic acid, chlorambucil, cidofovir, cilastatin, cilazapril, cinoxacin, ciprofloxacin, cisatracurium besilate, clavulanic acid, clodronic acid, clorazepate, cromoglicic acid, desmeninol, diclofenac, dicloxacillin, enoxacin, eprosartan, etacrynic acid, etidronic acid, etofylline, etomidate, felbinac, felodipine, fenofibrate, fexofenadine, flavoxate, fleroxacin, flucloxacillin, flufenamic acid, flumazenil, flupirtine, flurbiprofen, fluvastatin, fosfomycin, fosinopril, furosemide, fusidic acid, gabapentine, gemfibrozil, ibandronic acid, ibuprofen, iloprost, imidapril, imipenem, indomethacin, irinotecan, isradipine, ketoprofen, lercanidipine, levodopa, levofloxacin, liothyronine, lipoic acid, lisinopril, lodoxamide, lomefloxacin, lonazolac, loracarbef, loratadine, lovastatin, mefenamic acid, meropenem, mesalazine, metamizole, methotrexate, methyldopa, mezlocillin, moexipril, montelukast, moxifloxacin, mupirocin, naproxen, natamycin, nateglinide, nedocromil, nicotinic acid, nifedipine, nilvadipine, nimodipine, nisoldipine, nitrendipine, norfloxacin, ofloxacin, olsalazine, orotic acid, oxacillin, pamidronic acid, pangamic acid, penicillamine, phenoxymethylpenicillin, pentosan polysulfate, perindopril, pethidine, pipemidic acid, piperacillin, pirenoxine, piretanide, probenecid, proglumide, propicillin, prostaglandins, quinapril, quinaprilate, ramipril, repaglinide, reserpine, risedronic acid, salicylic acid, sulfasalazine, spirapril, sulbactam, sulfasalazine, sultamicillin, tazarotene, tazobactam, telmisartan, tiagabine, tiaprofenic acid, tilidine, tiludronic acid, trandolapril, tranexamic acid, valproic acid, vigabatrine, vincamine, vinpocetine, zanamivir, zoledronic acid, zopiclone and/or salts, isomers and/or combinations thereof are present.

Copolymer (b)

The copolymers (a) consist essentially or entirely of free-radical polymerized C1 to C4 esters of acrylic or methacrylic acid and further (meth)acrylate monomers which have functional tertiary amino groups.

Suitable monomers having functional tertiary amino groups are listed in U.S. Pat. No. 4,705,695, column 3, line 64 to column 4, line 13. Particular mention may be made of dimethylaminoethyl acrylate, 2-dimethylaminopropyl acrylate, dimethylaminopropyl methacrylate, dimethyl-aminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate and diethylamino-2,2-dimethyl)propyl methacrylate. Dimethylamihoethyl methacrylate is particularly preferred.

The content of monomers with tertiary amino group in the copolymer can advantageously be between 30 and 70% by weight, preferably between 40 and 60% by weight. The proportions of C1 to C4 esters of acrylic or methacrylic acid is 70-30% by weight. Mention should be made of methyl methacrylate, ethyl methacrylate, butyl methacrylate, methyl acrylate, ethyl acrylate, butyl acrylate.

A (meth)acrylate copolymer with tertiary amino groups corresponding to component (b) may be composed for example of 20-30% by weight methyl methacrylate, 20-30% by weight butyl methacrylate and 60-40% by weight dimethylaminoethyl methacrylate. The proportion of component (a) in the formulation is preferably 50-90% by weight.

Copolymers (b) are obtained in a manner known per se by free-radical bulk, solution, bead or emulsion polymerization. They must be brought before processing to the suitable particle size range by suitable grinding, drying or spraying processes. Granules and powders are suitable. Suitable commercial products are, for example, Eudragit® E 100 (granules) or Eudragit® E PO (powder).

Component (c)

Component (c) 5 to 50, preferably 10 to 20, % by weight (based on the copolymer component (b) of a $C_{12}$ to $C_{22}$ carboxylic acid. Component (c) is important for the processability. Unbranched $C_{12}$ to $C_{22}$ monocarboxylic acids are preferred. Branched derivatives of said substances may also be suitable where appropriate.

$C_{12}$ to $C_{22}$ monocarboxylic acids are, for example, in particular lauric acid and myristic acid. Palmitic acid and stearic acid are preferred.

Emulsifiers Having an HLB of at Least 14

Emulsifiers having an HLB of at least 14 should be present to the extent of less than 3% by weight, preferably less than 2 or 1% by weight; in particular, no such emulsifier should be present. The reason for this is the powder structure of the starting material in which the intrinsic taste of such emulsifiers is particularly evident. Surprisingly, in contrast to the teaching of WO 02/67906, it is possible to dispense with the use of emulsifiers on application of the specific method of the invention.

Emulsifiers or surfactants are surface-active substances with lyobipolar character, i.e. nonpolar, lipophilic and polar, hydrophilic centers must be present in their molecule (P.H. List, Azneiformenlehre, Wissenschaftliche Verlagsgesellschaft mbH Stuttgart, 1982, chapter 6.2.). Depending on the molecular structure, a distinction is made between ionic and nonionic emulsifiers.

The HLB is a measure, introduced by Griffin in 1950, of the hydrophilicity or lipophilicity of nonionic surfactants. It can be determined experimentally by the phenol titration method of Marszall; cf. "Parfümerie, Kosmetik", volume 60, 1979, pp. 444-448; further references in Römpp, Chemie-Lexikon, 8th edition, 1983, p. 1750. See also, for example, U.S. Pat. No. 4,795,643 (Seth)).

An HLB (hydrophilic/lipophilic balance) can be determined exactly only for nonionic emulsifiers. With anionic emulsifiers it is possible to determine this value by calculation, but it is virtually always above or far above 14.

Emulsifiers having an HLB above 14 are understood to be hydrophilic, nonionic emulsifiers with HLB range of at least 14, and likewise hydrophilic, anionic emulsifiers and salts thereof which have a calculated HLB above 14. Examples of emulsifiers having an HLB above 14 are, for example, sodium lauryl sulfate and sodium cetylstearyl sulfate, sucrose stearate and polysorbate 80.

Emulsifiers having HLB values of less than 14, such as, for example, glycerol monostearate, may on the other hand also be present in amounts of more than 3% by weight.

Excipients Customary in Pharmacy

The powder is incorporated into a water-soluble matrix of excipients customary in pharmacy.

Fillers and Binding Agents

The water-soluble matrix is predominantly formed of fillers and binding agents. These are preferably, for example, water-soluble mono-, di, oligo- or polysaccharides or derivatives thereof, also peptides, proteins etc. Examples are, for example, lactose, fructose, glucose, dextrose, galactose, mannitol, rhamnose, tragacanth, dextrin, guar gum, sorbitol, xylitol, isomatose, sucrose, maltose, hydroxypropyl-methylcellulose (HPMC), starch hydrolyzates, gelatin.

The amounts employed and the use of the customary additives in pharmaceutical coverings or coatings are familiar to the skilled worker. Customary additives may be, for example, release agents, pigments, stabilizers, antioxidants, pore formers, penetration promoters, aromatizing substances or flavorings. They serve as processing aids and are intended to ensure a reliable and reproducible production method and good long-term storage stability, or they achieve additional advantageous properties in the pharmaceutical form.

Release Agents:

Release agents usually have lipophilic properties and are usually added to spray suspensions. They prevent agglomeration of the cores during film coating. Those preferably employed are talc, Mg stearate or Ca stearate, ground silica, kaolin or nonionic emulsifiers having an HLB of between 3 and 8. The usual amounts employed of release agents in the coating and binding agents of the invention are between 0.1 to 10% by weight based on the pharmaceutical form.

Pigments:

Addition takes place only rarely in the form of the soluble dye. Usually aluminum or iron oxide pigments are dispersed. The amounts of pigments normally employed in the coating and binding agents of the invention are between 1 and 10% by weight, based on the pharmaceutical form.

Of course, all the substances employed must be toxicologically acceptable and usable in medicaments without risk for patients.

Further additives may also be plasticizers. Usual amounts are between 0 and 50, preferably 0 to 20, in particular 0 to 10, % by weight. However, it is particularly preferred for not more than 5% by weight or no plasticizer to be present, because the formulations are often sufficiently elastic merely through the presence of components (c), and additional plasticizer may lead to unwanted tackiness.

Plasticizers:

Plasticizers may influence the functionality of the polymer layer, depending on the type (lipophilic or hydrophilic) and amount added. Plasticizers achieve through physical interaction with the polymer a reduction in the glass transition temperature and promote film formation, depending on the amount added. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, succrose esters, sorbitan esters, diethyl sebacate, dibutyl sebacate and polyethylene glycols 200 to 12 000. Preferred plasticizers are triethyl citrate (TEC), acetyl triethyl citrate (ATEC) and dibutyl sebacate (DBS). Mention may moreover be made of esters which are usually liquid at room temperature, such as citrates, phthalates, sebacates or castor oil. Esters of citric acid and sebacic acid are preferably used. It is also possible to employ mixtures of plasticizers.

The Production Methods

The method of the invention provides for the production of an oral pharmaceutical form with immediate disintegration and active ingredient release even in the mouth, through vigorous mixing of components (a), (b) and (c) in the melt. Suitable processing temperatures are in the range from 80 to 200° C., preferably from 100 to 180° C. A twin-screw extruder is preferably employed for the purpose of vigorous mixing in the melt. After the solidification, the mixture is ground to an active ingredient-containing powder. The average particle size of the powder should be 200 μm or less, preferably from 50 to 150 μm.

The average particle size of the powders can be determined as follows: by air jet sieving to divide up the ground product easily into a few fractions. This method is somewhat less accurate than the alternatives in this measurement range. At least 70, preferably 90, % of the particles, based on mass (mass distribution), should be in the size range according to the invention of 200 μm or less, preferably from 50 to 150 μm. A very suitable measurement method is laser diffraction to determine the particle size distribution. Commercially available apparatuses permit measurement in air (Malvern S3.01 particle sizer) or preferably in liquid media (LOT, Galai CIS 1). A precondition for measurement in liquids is that the polymer does not dissolve therein or the particles change in another way during the measurement. A suitable medium is, for example, a highly dilute (approx. 0.02% strength) aqueous polysorbate 80 solution.

The active ingredient-containing powder can be processed to a tablet, suckable tablet, freeze-dried tablets, cast tablets or pastilles, sachets, chewable tablets, powders for reconstitution, lozenges and/or liquid-filled lozenges.

This processing usually takes place in a plurality of steps. Firstly, the active ingredient-containing copolymer powder is mixed with pharmaceutical excipients and can for example be compressed directly to tablets, suckable tablets or chewable tablets. The mixture can also be made into a paste with water, packed into a mold and freeze dried to result in freeze-dried tablets. Cast tablets or pastilles can be obtained by mixing the active ingredient-containing copolymer powder, e.g. with a saccharide solution at elevated temperature, pouring into a mold, e.g. for tablets or lozenges, and allowing to solidify by cooling. Liquid-filled lozenges can be produced by injecting a liquid mixture comprising the active ingredient-containing copolymer powder, e.g. in a sugar solution, into a solid casing composed for example of a sugar, and subsequently closing the latter.

Active Ingredient-Containing Powder

The active ingredient-containing powder has an average particle size of 200 μm or less, preferably from 50 to 150 μm and comprises
(a) an anionic active pharmaceutical ingredient which is in the form of a solid solution and is incorporated into
(b) a copolymer which consists of free-radical polymerized $C_1$ to $C_4$ esters of acrylic or methacrylic acid and further (meth)acrylate monomers which have functional tertiary amino groups, and
(c) 5 to 50% by weight, based on (b), of a $C_{12}$ to $C_{22}$ carboxylic acid,
(d) with the proviso that less than 3% by weight, based on the copolymer, or no emulsifier having an HLB of at least 14 is present.

Uses

The active ingredient-containing powder can be used to produce an oral pharmaceutical form with immediate disintegration and active ingredient release even in the mouth, which causes no bitter taste for at least 30 seconds after release. The pharmaceutical form may be in the form of compressed tablets or suckable tablets, freeze-dried tablets, cast tablets or pastilles, sachets, chewable tablets, powders for reconstitution, lozenges and/or liquid-filled lozenges.

Bitterness Values

The taste masking can be tested in a simple manner organoleptically by tasting. In this test, no or slightly bitter taste should be perceptible for at least 30 seconds after active ingredient release. Determination of bitterness values is more accurate. No or slightly bitter taste corresponds to bitterness values below 1000.

Bitterness values can be determined by DAB 1999 method 2.8.N8 (determination of the bitterness value).

Whereas, for example, ibuprofen has a bitterness value of around 100 000, the value according to the invention for an incorporated anionic active ingredient is usually below 1000, preferably below 100. A bitterness value of 1000 is usually sufficient for pharmaceutical practice.

EXAMPLES

Copolymers Used in the Examples:

Eudragit® E PO: copolymer powder composed of methyl methacrylate, butyl methacrylate, and dimethylamino-ethyl methacrylate in the ratio 25:25:50 with an average particle size of 15 μm.

Eudragit® E 100: copolymer of methyl methacrylate, butyl methacrylate, and dimethylaminoethyl methacrylate in the ratio 25:25:50 in granular form.

The effectiveness of the taste masking was tested organoleptically by tasting. This entailed ascertaining the time between putting in the mouth and occurrence of the bitter taste.

Example 1

Compound with 1 mol of dimethylaminoethyl methacrylate units contained in the copolymer Eudragit® E PO: 1 mol of stearic acid: 0.66 mol of ibuprofen: 0.18 mol of talc.

39.42 g of Eudragit® E PO, 35.2 g of stearic acid, 16.9 g of ibuprofen and 8.4 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it does not taste bitter after 2 min.

Example 2

Compound with 1 mol of dimethylaminoethyl methacrylate units contained in the copolymer Eudragit® E PO: 0.5 mol of stearic acid: 0.66 mol of ibuprofen: 0.18 mol of talc.

47.85 g of Eudragit® E PO, 21.38 g of stearic acid, 20.5 g of ibuprofen and 10.25 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it does not taste bitter or tastes slightly bitter after 2 min.

Example 3

Compound with 1 mol of dimethylaminoethyl methacrylate units contained in the copolymer Eudragit® E PO: 0.65 mol of stearic acid: 0.65 mol of ibuprofen: 0.18 mol of talc.

44.8 g of Eudragit® E PO, 26.4 g of stearic acid, 19.2 g of ibuprofen and 9.6 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes slightly bitter after 1 min.

Example 4

Compound with 1 mol of dimethylaminoethyl methacrylate units contained in the copolymer Eudragit® E PO: 0.33 mol of stearic acid: 0.66 mol of ibuprofen: 0.18 mol of talc.

51.6 g of Eudragit® E PO, 15.23 g of stearic acid, 22.1 g of ibuprofen and 11 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes slightly bitter after 1 min.

Example 5

Compound with 1 mol of dimethylaminoethyl methacrylate units contained in the copolymer Eudragit® E PO: 0.34 mol of stearic acid: 1 mol of ibuprofen: 0.27 mol of talc.

34.73 g of Eudragit® E PO, 15.52 g of stearic acid, 33.1 g of ibuprofen and 16.58 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 1 min.

Comparative Example 6

Active Ingredient Caffeine not According to the Invention

Compound with 1 mol of dimethylaminoethyl methacrylate units contained in the copolymer Eudragit® E PO: 0.5 mol of stearic acid: 1.58 mol of caffeine (m.p.: 234-239° C.).

41.47 g of Eudragit® E PO, 18.53 g of stearic acid, 40 g of caffeine were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 10 s.

Comparative Example 7

Without Stearic Acid

Compound with 1 mol of dimethylaminoethyl methacrylate units contained in the copolymer Eudragit® E PO: 0.67 mol of ibuprofen: 0.18 mol of talc.

60 g of Eudragit® E PO, 26.4 g of ibuprofen and 13.2 g of talc were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 10 s.

Comparative Example 8

Active Ingredient Paracetamol Not According to the Invention

Compound with 1 mol of dimethylaminoethyl methacrylate units contained in the copolymer Eudragit® E PO: 0.5 mol of stearic acid: 2.03 mol of paracetamol (m.p.: 168-172° C.).

41.47 g of Eudragit® E PO, 18.53 g of stearic acid, 40 g of paracetamol were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter immediately.

Comparative Example 9

Active Ingredient Paracetamol Not According to the Invention

Compound with 1 mol of dimethylaminoethyl methacrylate units contained in the copolymer Eudragit® E: 0.5 mol of stearic acid: 1 mol of paracetamol.

41.5% Eudragit® E 100, 18.53% stearic acid and 40% paracetamol were extruded together in an 18 mm twin-screw extruder in a temperature range from 100° C. to 172° C. In the zone of the extruder held at 0.172° C., the screw was designed to mix particularly vigorously in order to achieve a homogeneous melt.

The compound produced in this way tastes bitter immediately.

Example 10

Compound with 1 mol of dimethylaminoethyl methacrylate units contained in the copolymer Eudragit® E PO: 0.06 mol of stearic acid: 0.77 mol of ibuprofen.

100 g of Eudragit® E PO, 5 g of stearic acid and 50 g of ibuprofen were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 30-60 s min.

Example 11

Compound with 1 mol of dimethylaminoethyl methacrylate units contained in the copolymer Eudragit® E PO: 0.12 mol of stearic acid: 0.77 mol of ibuprofen.

100 g of Eudragit® E PO, 10 g of stearic acid and 50 g of ibuprofen were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 1 min.

Comparative Example 12

$C_{12}$ Alcohol Compound Instead of Stearic Acid

Compound with 1 mol of dimethylaminoethyl methacrylate units contained in the copolymer Eudragit® E PO: 0.34 mol of dodecanol: 0.77 mol of ibuprofen.

100 g of Eudragit® E PO, 20 g of dodecanol and 50 g of ibuprofen were weighed out and put together into an IKA measuring kneader preheated to 100° C., where the mixture was kneaded at a product temperature of 100° C. for 20 min at 60 rpm (2 kneading blades). The mixture was removed from the measuring kneader and cooled with dry ice.

If 1 g of this compound is put into the mouth, it tastes bitter after 20 s and has the unpleasant taste of dodecanol.

The invention claimed is:

1. A method for producing a pharmaceutical composition that when placed in the mouth immediately disintegrates releasing active ingredient (a) comprising:
   vigorously mixing
   (a) an anionic active pharmaceutical ingredient with
   (b) a copolymer consisting of free-radical polymerized $C_1$ to $C_4$ esters of acrylic or methacrylic acid and further (meth)acrylate monomers which have functional tertiary amino groups,
   (c) 5 to 50% by weight, based on (b), of a $C_{12}$ to $C_{22}$ carboxylic acid, and
   (d) 0.1 to 10% by weight, based on the weight of the powder, of a release agent selected from the group consisting of talc, Mg stearate or Ca stearate, ground silica, kaolin or nonionic emulsifiers having an HLB of between 3 and 8
   in a melt,
   solidifying the mixture, and
   grinding to an active ingredient-containing powder with an average particle size of 200 μm or less,
   incorporating the powder into a water-soluble matrix of at least one pharmaceutically acceptable excipient, with the proviso that not more than 3% by weight, based on the copolymer (b) of emulsifiers having an HLB of at least 14 may be present.

2. The method as claimed in claim 1, wherein a twin-screw extruder is employed for the purpose of vigorous mixing in the melt.

3. The method as claimed in claim 1, wherein extrusion takes place at temperatures in the range from 80 to 200° C.

4. The method as claimed in claim 1, wherein the incorporation of the powder into the water-soluble matrix takes place by compression, casting, granulation or freeze drying.

5. A powder with an average particle size of 200 μm or less, comprising:
   (a) an anionic active pharmaceutical ingredient,
   (b) a copolymer which consists of free-radical polymerized $C_1$ to $C_4$ esters of acrylic or methacrylic acid and further (meth)acrylate monomers which have functional tertiary amino groups,
   (c) 5 to 50% by weight, based on (b), of a $C_{12}$ to $C_{22}$ carboxylic acid,
   (d) 0.1 to 10% by weight, based on the weight of the powder, of a release agent selected from the group consisting of talc, Mg stearate or Ca stearate, ground silica, kaolin or nonionic emulsifiers having an HLB of between 3 and 8,
   with the proviso that less than 3% by weight, based on the copolymer (b), of an emulsifier having an HLB of at least 14 is present,
   wherein said powder when placed in the mouth immediately disintegrates and releases active ingredient (a); and
   wherein said powder is produced by vigorously mixing
   (i) the anionic active pharmaceutical ingredient with
   (ii) the copolymer consisting of free-radical polymerized $C_1$ to $C_4$ esters of acrylic or methacrylic acid and further (meth)acrylate monomers which have functional tertiary amino groups,
   (iii) the release agent selected from the group consisting of talc, Mg stearate or Ca stearate, ground silica, kaolin or nonionic emulsifiers having an HLB of between 3 and 8, and
   (iv) 5 to 50% by weight, based on (b), of said $C_{12}$ to $C_{22}$ carboxylic acid, in a melt, solidifying the mixture, and grinding to an active ingredient-containing powder with an average particle size of 200 μm or less.

6. The powder of claim 5, wherein (a) comprises an anionic analgesic, an anionic antirheumatic, or an anionic antibiotic.

7. The powder of claim 5, wherein the anionic active pharmaceutical ingredient (a) is ibuprofen.

8. The powder of claim 5, wherein said anionic active pharmaceutical ingredient (a) has been incorporated into said copolymer (b).

9. The powder of claim 5, wherein copolymer (b) is a copolymer of methyl methacrylate, butyl methacrylate, and dimethylaminoethyl methacrylate.

10. The powder of claim 5, wherein carboxylic acid (c) is at least one of lauric acid, myristic acid, palmitic acid, and stearic acid.

11. The powder of claim 5 that contains no emulsifier having an HLB (hydrophilic/lipophilic balance) of 14 or more.

12. The powder of claim 5 that contains from 1 to less than 3% by weight, based on the copolymer, of an emulsifier having an HLB (hydrophilic/lipophilic balance) of 14 or more.

13. The powder of claim 5 that contains from 1-2% of an emulsifier having an HLB (hydrophilic/lipophilic balance) of 14 or more.

14. The powder of claim 5, which has a bitterness value determined by DAB 1999 method 2.8.N8 below 1,000 for at least 30 seconds after release of the active ingredient (a).

15. A pharmaceutical composition comprising the powder of claim 5 and at least one pharmaceutically acceptable excipient.

16. The pharmaceutical composition of claim 15, wherein said at least one excipient is a release agent having an HLB between 3 and 8.

17. The pharmaceutical composition of claim 15, wherein said at least one excipient is a plasticizer having a molecular weight ranging between 100 and 20,000 and which comprises at least one hydrophilic group.

18. The pharmaceutical composition of claim 15 in the form of a compressed tablet, suckable tablet, freeze-dried tablet, cast tablet, pastilles, sachet, chewable tablet, powder for reconstitution, lozenge and/or liquid-filled lozenge.

19. The pharmaceutical composition of claim 15 which is produced by:

vigorously mixing (a) an anionic active pharmaceutical ingredient with (b) a copolymer consisting of free-radical polymerized $C_1$ to $C_4$ esters of acrylic or methacrylic acid and further (meth)acrylate monomers which have functional tertiary amino groups, and (c) 5 to 50% by weight, based on (b), of a $C_{12}$ to $C_{22}$ carboxylic acid in a melt with no emulsifier having an HLB or at least 14, solidifying the mixture, grinding to an active ingredient-containing powder with an average particle size of 200 μm or less, and incorporating the powder into a water-soluble matrix of at least one pharmaceutically acceptable excipient.

* * * * *

UNITED STATES PATENT AND TRADEMARK OFFICE
CERTIFICATE OF CORRECTION

PATENT NO. : 8,343,542 B2
APPLICATION NO. : 10/542283
DATED : January 1, 2013
INVENTOR(S) : Hans-Ulrich Petereit et al.

It is certified that error appears in the above-identified patent and that said Letters Patent is hereby corrected as shown below:

On the title page, Item (73), the Assignee's information is incorrect. Item (73) should read:

-- (73) Assignee: Evonik Roehm GmbH, Darmstadt (DE) --

Signed and Sealed this
Fifth Day of March, 2013

Teresa Stanek Rea
*Acting Director of the United States Patent and Trademark Office*